United States Patent
Spievack

(10) Patent No.: US 6,783,776 B2
(45) Date of Patent: Aug. 31, 2004

(54) TISSUE REGENERATIVE COMPOSITION, METHOD OF MAKING, AND METHOD OF USE THEREOF

(75) Inventor: Alan R. Spievack, Cambridge, MA (US)

(73) Assignee: ACell, Inc., Cambridge, MA (US)

( * ) Notice: Subject to any disclaimer, the term of this patent is extended or adjusted under 35 U.S.C. 154(b) by 0 days.

(21) Appl. No.: 10/280,678

(22) Filed: Oct. 25, 2002

(65) Prior Publication Data

US 2003/0059407 A1 Mar. 27, 2003

Related U.S. Application Data

(63) Continuation of application No. 09/691,345, filed on Oct. 18, 2000, now Pat. No. 6,576,265.
(60) Provisional application No. 60/171,733, filed on Dec. 22, 1999.

(51) Int. Cl.[7] ............................................. A61K 35/30
(52) U.S. Cl. ..................................... 424/558; 623/23.72
(58) Field of Search ................................. 424/551, 558; 623/13, 17, 23.72

(56) References Cited

U.S. PATENT DOCUMENTS

| | | | |
|---|---|---|---|
| 2,127,903 A | 8/1938 | Bowen | 128/334 |
| 3,562,820 A | 2/1971 | Braun | 3/1 |
| 4,801,299 A | 1/1989 | Brendel et al. | 623/1 |
| 4,902,508 A | 2/1990 | Badylak et al. | 424/95 |
| 4,956,178 A | 9/1990 | Badylak et al. | 424/551 |
| 5,275,826 A | 1/1994 | Badylak et al. | 424/551 |
| 5,281,422 A | 1/1994 | Badylak et al. | 424/551 |
| 5,336,616 A | 8/1994 | Livesey et al. | 435/240.2 |
| 5,352,463 A | 10/1994 | Badylak et al. | 424/551 |
| 5,372,821 A | 12/1994 | Badylak et al. | 424/551 |
| 5,445,833 A | 8/1995 | Badylak et al. | 424/551 |
| 5,480,424 A | 1/1996 | Cox | 623/2 |
| 5,516,533 A | 5/1996 | Badylak et al. | 424/551 |
| 5,543,894 A | 8/1996 | Carolan | 355/208 |
| 5,554,389 A | 9/1996 | Badylak et al. | 424/558 |
| 5,573,784 A | 11/1996 | Badylak et al. | 424/551 |
| 5,641,518 A | 6/1997 | Badylak et al. | 424/551 |
| 5,695,998 A | 12/1997 | Badylak et al. | 435/391 |
| 5,711,969 A | 1/1998 | Patel et al. | 424/551 |
| 5,755,791 A | 5/1998 | Whitson et al. | 623/15 |
| 5,762,966 A | 6/1998 | Knapp, Jr. et al. | 424/551 |
| 5,866,414 A | 2/1999 | Badylak et al. | 435/325 |
| 5,885,619 A | 3/1999 | Patel et al. | 424/551 |
| 5,891,617 A | 4/1999 | Watson et al. | 435/1.3 |
| 5,899,936 A | 5/1999 | Goldstein | 623/2 |
| 5,916,266 A | 6/1999 | Yui et al. | 623/11 |
| 6,087,157 A | 7/2000 | Badylak et al. | 435/289.1 |
| 6,096,347 A | 8/2000 | Geddes et al. | 424/551 |
| 6,126,686 A | 10/2000 | Badylak et al. | 623/1.24 |
| 6,322,593 B1 | 11/2001 | Pathak et al. | 623/23.72 |
| 6,376,244 B1 | 4/2002 | Atala | 435/376 |
| 6,432,712 B2 | 8/2002 | Wolfinbarger, Jr. et al. | 435/395 |
| 6,455,311 B1 | 9/2002 | Vacanti | 435/395 |
| 6,485,723 B1 | 11/2002 | Badylak et al. | 424/93.7 |
| 6,485,969 B1 | 11/2002 | Asem et al. | 435/325 |
| 6,576,265 B1 * | 6/2003 | Spievack | 424/551 |
| 6,579,538 B1 * | 6/2003 | Spievack | 424/558 |
| 2003/0054022 A1 * | 3/2003 | Spievack | 424/423 |
| 2003/0059404 A1 * | 3/2003 | Spievack | 424/93.7 |
| 2003/0059410 A1 * | 3/2003 | Spievack | 424/93.7 |
| 2003/0064111 A1 * | 4/2003 | Spievack | 424/551 |

FOREIGN PATENT DOCUMENTS

| | | | |
|---|---|---|---|
| WO | 98/22158 | 5/1998 | A61L/27/00 |
| WO | 98/25637 | 6/1998 | A61K/35/407 |
| WO | 98/25545 | 8/1998 | A61F/2/06 |
| WO | 98/25546 | 8/1998 | A61F/2/06 |
| WO | 00/15765 | 3/2000 | |

OTHER PUBLICATIONS

Badylak et al., "Small intestine submucosa: a substrate for in vitro cell growth," *J. Biomat. Science* 9:863–878 (1998).

Badylak et al., "Endothelial cell adherence to small intestinal submucosa; an acellular bioscaffold,"*Biomaterials* 20:2257–2263 (1999).

Lindberg et al., "Porcine small intestinal submucosa (SIS): a bioscaffold supporting in vitro primary human epidermal cell differentiation and synthesis of basement membrane proteins, " *Burns* 27:254–266 (2001).

Peel et al., "Formation of a SIS–cartilage composite graft in vitro and its use in the repair of articular cartilage defects, "*Tissue Eng.* 4:143–155 (1998).

Voytik–Harbin et al., "Small intestinal submucosa: A tissue derived extracellular matrix that promotes tissue–specific growth and differentiation of cells in vitro,"*Tissue Eng.* 4:157–174 (1998).

Voytik–Harbin et al., "Three–dimensional imaging of extracellular matrix and extracellular matrix–cell interactions, "*Methods Cell Biol.* 63:583–597 (2001).

Voytik–Harbin et al., "Three–dimensional extracellular matrix substrates for cell culture,"*Methods Cell Biol.*63:561–581 (2001).

Yoo et al., "Bladder Augmentation using Allogenic Bladder Submucosa Seeded with Cells,"*Urology* 51(2):221–225 (1998).

Hadlock et al., "A New Artificial Nerve Graft Containing Rolled Schwann Cell Monolayers,"*Microsurgery* 21:96–101 (2001).

Lakey et al., "Improved Islet Survival and In Vitro Function Using Small Intestinal Submucosa,"*Transplantation Proceedings* 30:383 (1998).

(List continued on next page.)

Primary Examiner—James Ketter
(74) Attorney, Agent, or Firm—Testa Hurwitz & Thibeault LLP

(57) ABSTRACT

A matrix, including epithelial basement membrane, for inducing repair of mammalian tissue defects and in vitro cell propagation derived from epithelial tissues of a warm-blooded vertebrate.

35 Claims, 2 Drawing Sheets

OTHER PUBLICATIONS

Pariente et al., "In Vitro Biocompatibility Evaluation of Naturally Derived and Synthetic Biomaterials using Normal Human Bladder Smooth Muscle Cells,"*The Journal of Urology* 167:1867–1871 (2002).

Pariente et al., "In Vitro Biocompatibility Assessment of Naturally Derived and Synthetic Biomaterials using Normal Human Urothelial Cells,"*J. Biomed. Mater. Res.* 55:33–39 (2001).

Rosenthal et al., "The Mucosal Invasion Model, "*Arch Otolaryngol. Head Neck Surgery* 127:1467–1470 (2001).

Zhang et al., "Coculture of Bladder Urothelial and Smooth Muscle Cells on Small Intestine Submucosa: Potential Applications for Tissue Engineering Technology,"*The Journal of Urology* 164:928–935 (2000).

Swiatek, "Charges fly in biomaterial feud", Indystar.com., pp. 1–3, (2004).

Cook et al. v. ACell et al. (N.D. Ind.; 03–0046), 2 Binders.

Dahms et al., "Bladder Acellular Matrix Graft in Rats: Its Neurophysiologic Properties and mRNA Expression of Growth Factors TGF–a and TGF–b,"*Neurourology and Urodynamics* 17:37–54 (1998).

Dahms et al., "Composition and biomechanical properties of the bladder acellular matrix graft: comparative analysis in rat, pig and human,"*British Journal of Urology* 82:411–419 (1998).

Dahms et al., "Free Ureteral Replacement in Rats: Regeneration of Ureteral Wall Components in the Acellular Matrix Graft,"*Urology* 50(5) 818–825 (1997).

Piechota et al., "Bladder acellular matrix graft: in vivo functional properties of the regenerated rat bladder,"*Urol Res* 27:206–213 (1999).

Piechota et al., "Functional rat bladder regeneration through xenotransplantation of the bladder acellular matrix graft, "*British Journal of Urology* 81:548–559 (1998).

Piechota et al., "In Vitro Functional Properties of the Rat Bladder Regenerated by the Bladder Acellular Matrix Graft, "*Journal of Urology* 159:1717–174 (1998).

Probst et al., "Homologous bladder augmentation in dog with the bladder acellular matrix graft,"*BJU International* 85:362–371 (2000).

* cited by examiner

TISSUE REGENERATIVE COMPOSITION, METHOD OF MAKING, AND METHOD OF USE THEREOF

CROSS-REFERENCE TO RELATED APPLICATIONS

This application is a continuation application of U.S. patent application Ser. No. 09/691,345, filed Oct. 18, 2000 now U.S. Pat. No. 6,576,265, which is based on and claims priority to U.S. provisional patent application Ser. No. 60/171,733, filed Dec. 22, 1999.

TECHNICAL FIELD

This invention relates to devitalized acellular tissue regeneration compositions, methods of making, and methods of use.

BACKGROUND OF THE INVENTION

Submucosal tissues of warm-blooded vertebrates are useful in tissue grafting materials. For example, submucosal tissue graft compositions derived from small intestine have been described in U.S. Pat. No. 4,902,508 (hereinafter the '508 patent) and U.S. Pat. No. 4,956,178 (hereinafter the '178 patent), and submucosal tissue graft compositions derived from urinary bladder have been described in U.S. Pat. No. 5,554,389 (hereinafter the '389 patent). All of these compositions consist essentially of the same tissue layers and are prepared by the same method, the difference being that the starting material is small intestine on the one hand and urinary bladder on the other. The procedure detailed in the '508 patent, incorporated by reference in the '389 patent and the procedure detailed in the '178 patent, includes mechanical abrading steps to remove the inner layers of the tissue, including at least the luminal portion of the tunica mucosa of the intestine or bladder, i.e., the lamina epithelialis mucosa (epithelium) and lamina propria, as detailed in the '178 patent. Abrasion, peeling, or scraping the mucosa delaminates the epithelial cells and their associated basement membrane, and most of the lamina propria, at least to the level of a layer of organized dense connective tissue, the stratum compactum. Thus, the tissue graft material previously recognized as soft tissue replacement material is devoid of epithelial basement membrane and consists of the submucosa and stratum compactum.

The epithelial basement membrane is a thin sheet of extracellular material contiguous with the basilar aspect of epithelial cells. Sheets of aggregated epithelial cells of similar type form an epithelium. Epithelial cells and their associated epithelial basement membrane are positioned on the luminal portion of the tunica mucosa and constitute the internal surface of tubular and hollow organs and tissues of the body. Epithelial cells and their associated epithelial basement membrane are also positioned on the external surface of the body, i.e., skin. Examples of a typical epithelium having a basement membrane include, but are not limited to the following: the epithelium of the skin, intestine, urinary bladder, esophagus, stomach, cornea, and liver.

Epithelial cells are positioned on the luminal or superficial side of the epithelial basement membrane, opposite to connective tissues. Connective tissues, the submucosa, for example, are positioned on the abluminal or deep side of the basement membrane. Examples of connective tissues that are positioned on the abluminal side of the epithelial basement membrane are the submucosa of the intestine and urinary bladder, and the dermis and subcutaneous tissues of the skin.

SUMMARY OF THE INVENTION

The present invention provides devitalized tissue regenerative compositions comprising an epithelial basement membrane as part of a matrix or scaffold for tissue repair or regeneration. The inclusion of the epithelial basement membrane in devitalized mammalian tissue regenerative compositions results in improved in vivo endogenous cell propagation and tissue restoration as compared to submucosal matrices described above which do not include an epithelial basement membrane. For the purposes of this invention, devitalized means acellular or substantially acellular. For the purposes of this invention, epithelial basement membrane means at least a portion of the intact epithelial basement membrane.

According to the invention, a preferred devitalized matrix for mammalian tissue repair or regeneration comprises at least a portion of a mammalian epithelial basement membrane, preferably the entire epithelial basement membrane, and the tunica propria that is immediately subjacent to the basement membrane. Devitalized matrices of the invention restore or replace diseased, defective, or missing tissue when placed in contact with host tissue. In a preferred embodiment, the invention comprises a devitalized matrix that is custom-shaped to conform to the diseased or defective tissue. In a particular embodiment, the matrix comprises a sheet of matrix derived from the urinary bladder, the intestine, or any other mammalian epithelial tissue. In another embodiment, the matrix is injectable by means of being transformed into a fine particulate, emulsion, gel or extract. A matrix of the invention may act as a carrier for a pharmaceutical agent. A preferred application of the matrix of the invention is the repair or restoration of cardiac tissue. In particular, a matrix or composition of the invention is useful to restore or replace at least a portion of a cardiac valve, the interatrial septum, the interventricular septum, or the myocardium. For the purposes of this invention, matrix and composition are interchangeable terms.

In one embodiment, the invention features a devitalized composition comprising epithelial basement membrane and tunica propria immediately subjacent to the basement membrane. The epithelial basement membrane and tunica propria immediately subjacent to the basement membrane are delaminated from cells of a mammalian epithelium and abluminal portions of the tunica propria. Mammalian epithelial tissue used in this aspect of the invention is preferably derived from urinary bladder, intestine, or any other mammalian epithelial tissue. Further embodiments feature a composition shaped to conform to a diseased or defective cardiac valve such as at least a portion of a pulmonic valve, aortic valve, right or left atrioventricular valve, or the myocardium.

In still another embodiment, the invention features a composition comprising epithelial basement membrane, tunica propria, and submucosa. The epithelial basement membrane and tunica propria are delaminated from the cells of an epithelium and from the tunica muscularis of a mammalian epithelial tissue.

In yet another embodiment, the invention features a composition comprising epithelial basement membrane, tunica propria, and smooth muscle cells of the tunica muscularis, all delaminated from epithelial cells of a mammalian epithelium.

The composition, according to the invention, is not limited to merely the embodiments enclosed. Rather, the composition, according to the invention, comprises one or more layers of an epithelial tissue in combination with at least a portion, preferably the entire, intact epithelial basement membrane.

In another aspect, the invention provides methods for inducing restoration or repair of diseased or defective cardiac tissue. A preferred method of the invention comprises the step of contacting a host tissue with a devitalized matrix derived from a mammal. The devitalized matrix comprises at least a portion of an epithelial basement membrane and tunica propria immediately subjacent to the basement membrane. In preferred embodiments, methods of the invention comprise inducing endogenous epithelial repair using tissue regenerative compositions of the invention.

BRIEF DESCRIPTION OF THE DRAWINGS

The drawings are not to scale and emphasis instead is generally being placed upon illustrating the principles of the invention.

DETAILED DESCRIPTION OF THE INVENTION

A devitalized tissue regenerative composition in accordance with the present invention comprises epithelial basement membrane or at least a portion of the epithelial basement membrane and at least the subjacent portion of the tunica propria harvested from a mammalian epithelial tissue. Preferred epithelial tissues for use in the invention include, but are not limited to, urinary bladder and other tissues of the uro-genital tract, small intestine, esophagus and other tissues of the gastrointestinal tract, skin, liver, and arteries such as the aorta and other tissues of the cardiovascular system. In a preferred embodiment, the invention provides a tissue graft composition comprising at least a portion of the epithelial basement membrane and subjacent tunica propria, separated from the luminal epithelial cells, the abluminal adventitial, serosal, and smooth muscle layers and the submucosal tissue layers Tissue separation or delamination techniques, according to the invention, provide a layer of devitalized extracellular matrix material including epithelial basement membrane or at least a portion of the epithelial basement membrane essentially free of cells. Any remaining cellular elements are then removed by further processing steps such as rinsing in hypotonic saline, peracetic acid or sterile water.

Figure 1A:
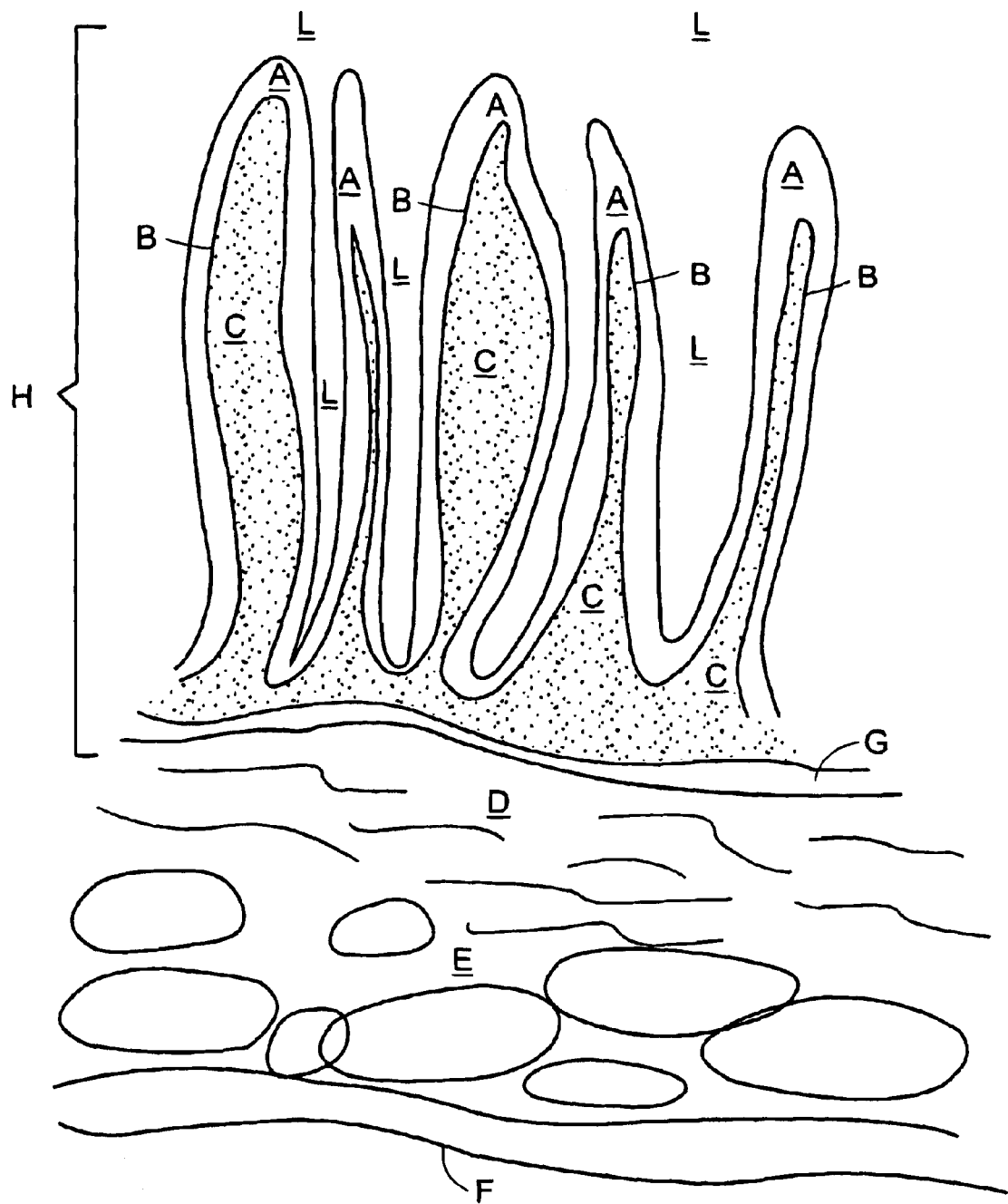
FIG. 1A is a cross-sectional view of the wall of the intestine.
Figure 1B:
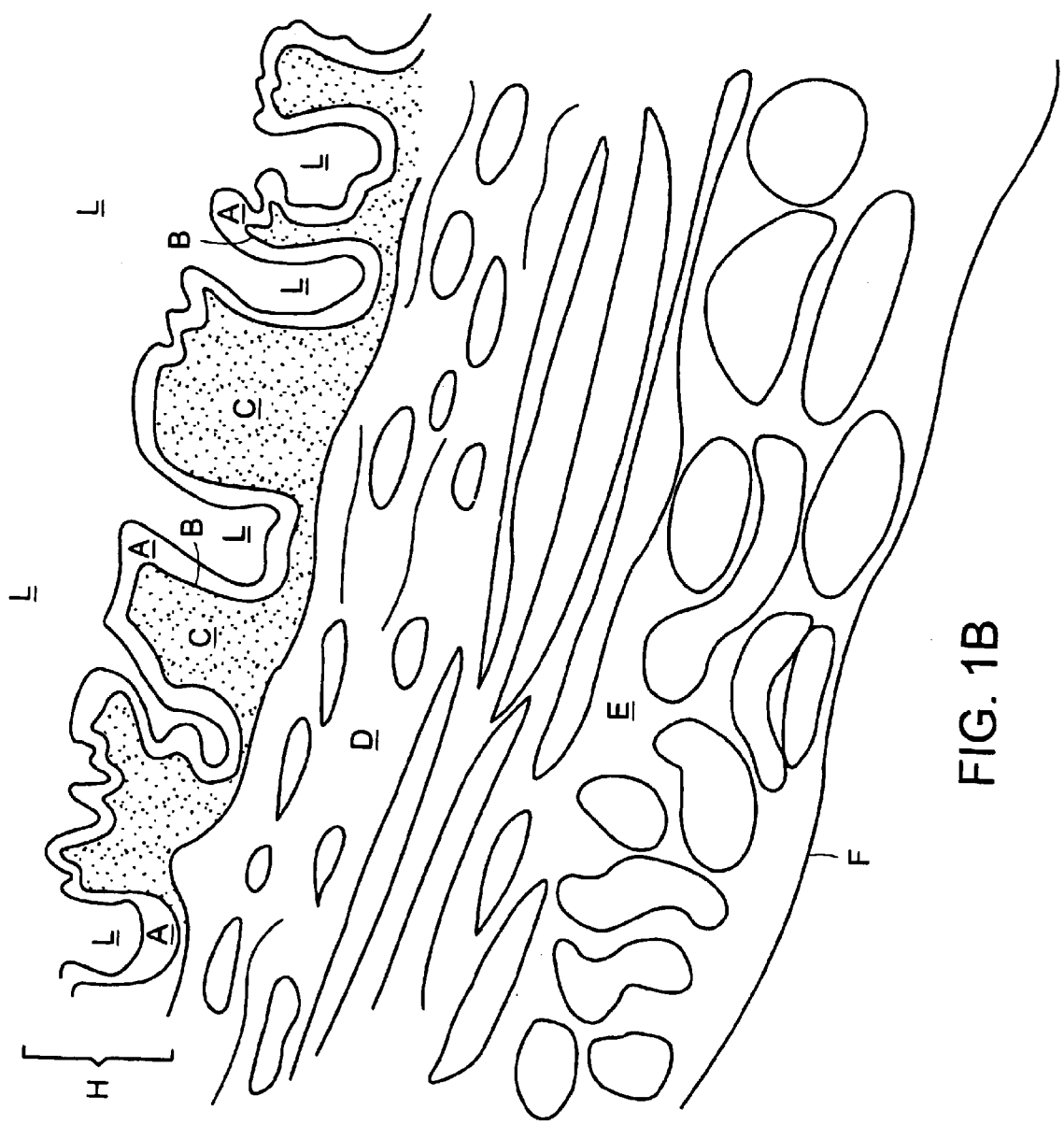
FIG. 1B is a cross-sectional view of the wall of the urinary bladder.

Accordingly, referring to FIGS. 1A and 1B, a preferred embodiment of the invention comprises epithelial basement membrane B and the biotropic connective tissue known as the tunica propria C that is immediately subjacent to and positioned on the abluminal side of the epithelial basement membrane B of the intestine illustrated in FIG. 1A, or the urinary bladder illustrated in FIG. 1B or any other epithelial tissue. This embodiment of the invention features the epithelial basement membrane B and portions of the tunica propria C adjacent to the epithelial basement membrane B. The epithelial basement membrane B and tunica propria C are delaminated from the epithelial cells A, the submucosa D, the tunica muscularis E, and the serosa F. Thus, in this embodiment of the invention, the portions of the tunica mucosa H adjacent the lumen L, i.e., the luminal portions of the tunica mucosa, form a preferred tissue matrix composition.

In another preferred embodiment, again referring to FIGS. 1A and 1B, a composition of the invention comprises epithelial basement membrane B, tunica propria C, and the tunica submucosa D. The epithelial basement membrane B, tunica propria C, and the tunica submucosa D are delaminated from the epithelial cells A, tunica muscularis E, and tunica serosa F. In this embodiment, the portions of the tunica mucosa H that include the epithelial basement membrane, and the tunica submucosa, form a preferred tissue matrix composition.

In yet another composition, a preferred embodiment of the invention comprises the epithelial basement membrane B, the tunica propria C that lie adjacent the epithelial basement membrane B, the tunica submucosa D and at least a portion of the tunica muscularis E.

Sources of Epithelial Tissue

Material for tissue regeneration compositions of the invention is typically prepared from tissue harvested from animals raised for meat production, including but not limited to, pigs, cattle and sheep. Other warm-blooded vertebrates are also useful as a source of tissue, but the greater availability of such tissues from animals used for meat production makes such tissue preferable. Thus, there are inexpensive commercial sources of tissue for use in preparation of the tissue compositions in accordance with the present invention. There may be specially bred or genetically engineered strains of certain species that are used as a tissue source. For example, pigs that are genetically engineered to be free of the galacatosyl, alpha 1,3 galactose (GAL epitope) may be used as the source of tissues for production of the composition. Alternatively, herds of pigs that are raised to be free of specific pathogens may be used as the source of tissues. Mammalian tissue used as the source of tissue for production of the composition of the invention may be harvested from an animal of any age group, including embryonic tissues, market weight, gender or stage of sexual maturity.

Tissue Sources of Epithelial Basement Membrane

Urinary Bladder

A preferred source of epithelial basement membrane is the urinary bladder illustrated in FIG. 1B of a warm-blooded vertebrate such as a pig. Superior biologic tissue remodeling properties are derived from epithelial basement membrane components that support and promote cell growth without invasion, and the subjacent tunica propria matrix material that allows and promotes endogenous cellular adhesion, invasion, growth and differentiation. The matrix, referred to hereinafter as urinary bladder matrix (UBM), includes the basement membrane B of the urinary bladder epithelium and the subjacent tunica propria C. In this embodiment, epithelial basement membrane B and the subjacent tunica propria C are delaminated from the epithelial cells A and the extracellular matrix of the tunica submucosa D, the tunica muscularis E, and the tunica serosa F. UBM is harvested from any warm-blooded vertebrate but is most preferably harvested from pigs. UBM is used as a bioscaffold for the repair or restoration of body tissues and organs such as musculoskeletal and cardiovascular structures, dermatologic and gastrointestinal tissues, urogenital and reproductive tissues, neurologic tissues, liver, kidney, and head and neck tissues.

A preferred UBM tissue regenerative composition comprises epithelial basement membrane, preferably urinary bladder basement membrane, and the biotropic molecular structure that lies immediately subjacent the epithelial basement membrane from the urinary bladder tissue of warm blooded vertebrates. In this embodiment, epithelial basement membrane is delaminated from the luminal epithelial cells, abluminal adventitial, serosal, and smooth muscle tissues, and submucosal tissues. Tissue graft compositions of the invention have remarkably superior tissue growth characteristics as compared to previously described submucosal tissue graft compositions implanted or injected into a vertebrate host to cause the repair or replacement of damaged, missing, or defective tissues or organs.

Methods of the present invention avoid complete loss of the epithelial basement membrane and result in a tissue regenerative composition that includes at least a portion of the epithelial basement membrane. In a preferred embodiment, the epithelial basement membrane as determined by conventional histochemical or immunohistochemical techniques and light, or electron microscopy, is largely intact. The resulting devitalized material obtained by methods of the present invention is in contrast to methods for making tissue graft compositions derived from small intestine and urinary bladder as described in the '508 and '389 patents which result in a graft material including submucosa exclusive of the epithelial basement membrane. Steps in preparation of UBM from urinary bladder tissue differ from previously described steps for preparation of submucosal tissue graft composition described in the '508 patent and the '389 patent. In the methods for the preparation of the submucosal tissue graft composition described in the '508 and '389 patents, the mucosa is mechanically removed by abrasion.

According to the present invention, UBM is prepared by removing the urinary bladder tissue from a warm-blooded vertebrate, for example, a pig, and delaminating the tissue by first soaking the tissue in a deepithelializing solution, for example, hypertonic saline, most preferably 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, submucosa and abluminal portion of the tunica propria are removed from the remaining deepithelialized tissue by mechanical abrasion or by a combination of enzymatic treatment, hydration, and abrasion. Mechanical removal of these tissues is accomplished by removal of mesenteric tissues with, for example, Adson-Brown forceps and Metzenbaum scissors and wiping away the tunica muscularis and abluminal tunica propria using a longitudinal wiping motion with a scalpel handle or other rigid object wrapped in moistened gauze. After these tissues are removed, the resulting tissue scaffold consists of epithelial basement membrane and subjacent tunica propria. This tissue differs from previously known tissue compositions derived from animal epithelial tissues by the inclusion of a largely intact epithelial basement membrane in the present invention. The tissues may be further processed by rinsing in hypertonic saline, peracetic acid or sterile water. Other methods for removing tissue layers, a microtome, for example, may also be used to obtain the tissue composition of the invention.

The method for preparation of tissue regenerative compositions according to the invention is not limited to the use of urinary bladder tissue as a starting material. The method according to the invention is also applicable to other starting tissues, for example, skin, esophagus, stomach, and intestinal tissues.

After preparing UBM according to the method of the invention, the resulting tissue scaffold consists of an approximately 10–120 micrometer thick material that consists primarily (i.e., greater than 90%) of extracellular matrix (ECM) including the epithelial basement membrane. This material may or may not retain some of the cellular elements that comprised the original tissue such as capillary endothelial cells or fibrocytes. These cellular elements are removed by subsequent exposure to peracetic acid as part of the disinfection of the biomaterial. The material differs in its histologic appearance and its architecture from the submucosal tissue graft compositions because of the smooth epithelial basement membrane that demarks the luminal surface and the dense, partially organized collagenous ECM that demarks the abluminal surface. The ECM material stains pink with H&E stain and blue with Masson's trichrome stain.

Skin, Esophagus

Similarly, steps used in preparation of tissue regenerative compositions from other epithelial organs having tissue layers similar to urinary bladder, such as skin, or esophagus, parallel the steps described above for preparing UBM. Like the urinary bladder matrix, the material remaining after removal of the epithelial cells, tunica serosa, tunica muscularis and abluminal tunica propria, includes at least a portion of the epithelial basement membrane, and the adjacent tunica propria.

Small Intestine

A tissue regenerative composition of the invention is also derived from epithelial tissues of the gastrointestinal tract, such as the small intestine. Steps in preparation of a tissue regenerative composition that includes at least a portion of the epithelial basement membrane of the small intestine and subjacent tunica propria, termed SIM, are similar to the steps described above for the formation of UBM. 1.0N saline may be used to remove the intestinal epithelial cells from the epithelial basement membrane. An alternate method for removing epithelial cells is to soak the epithelial tissue in a detergent such as a non-ionic detergent, for example, Triton X-100, at concentrations from 0.025 to 1%, for 5 minutes to several hours.

In one embodiment, the delaminated tissue regenerative composition derived from an epithelial tissue is stored either in a frozen hydrated state or is air dried at room temperature, then stored. Alternatively, the tissue regenerative composition is lyophilized and stored in a dehydrated state at either room temperature or frozen. In yet another embodiment, the tissue regenerative composition can be minced and fluidized by digesting the material in proteases, for example pepsin or trypsin, for periods of time sufficient to solubilize the tissue and form a substantially homogeneous solution. The viscosity of the solubilized material can be varied by adjusting the pH to create a gel, gel-sol, or completely liquid state. The preparation of fluidized intestinal submucosa, for example, is described in U.S. Pat. No. 5,275,826, expressly incorporated herein by reference.

In still another embodiment, the present invention contemplates the use of powder forms of the tissue regenerative composition. In one embodiment, a powder form of tissue regenerative composition is created by mincing or crushing the delaminated material to produce particles ranging in size from 0.005 mm$^2$ to 2.0 mm$^2$. The material, delaminated from unwanted tissue layers, is frozen for example, in liquid nitrogen, to perform the crushing procedure. Alternatively, the material is dehydrated to perform the crushing procedure. The crushed form of the material is then lyophilized to form a substantially anhydrous particulate tissue regenerative composition.

Tissue compositions of the present invention are suitable for many surgical and nonsurgical applications for the purpose of inducing reconstructive wound healing and tissue restoration. For example, they are used to replace damaged, diseased, or missing heart valves, arteries, veins, urinary bladder, liver, portions of the gastrointestinal tract, or they can be used as templates for repair or replacement of head and neck structures. The material, in any of a number of its solid or fluidized forms, can be used as a scaffold for dermal or epidermal repair, injected into various body sphincters such as urinary sphincter or esophageal or gastric sphincters, folded into a tube or partial tube as a conduit for the restoration of nervous tissue or extruded or molded into any shape suitable for its application as a tissue regenerative composition. The tissue regenerative composition of the invention can be sutured into place in its solid sheet form, placed in wounds or body locations in a gel form, or injected in its liquid or particulate form. Tissue compositions of the present invention induce growth of endogenous tissues including epithelial and connective tissues when target tissues in vivo are placed in contact with mammalian derived, devitalized tissue compositions comprising at least a portion of an epithelial basement membrane.

Urinary Bladder Matrix (UBM)

UBM compositions comprise at least type I and type IV collagen, glycosaminoglycans, including hyaluronic acid, chondroitin sulfate A and B, heparin and heparin sulfate. In addition, one or more of basic fibroblast growth factor, vascular endothelial cell growth factor and TGF-beta are present in UBM.

The physical properties of UBM have been partially characterized. UBM has a uniaxial strength of approximately 0.1–2.0 pound per 1.0 cm wide strip (measured with a material testing system machine via American Standards for Testing Materials pulling at 1 inch/minute). The suture retention strength of the material is approximately 1.0–4.0 Newtons (N) per sheet layer, specifically, 4–18 N for a 4 layer matrix and 30 N–120 N for a 30 layer matrix. The ball burst test failure force is approximately 4–10 pounds for each layer, specifically, 32–80 N for 8 layers, 16–40 N for 4 layers, and 36–120 N for 12 layers.

The porosity index is defined as the amount of water that flows through a material per $cm^2$/minute at 120 mmHg pressure. Water porosity differs from one side of UBM to the other depending on the direction of flow. Water flows from the epithelial basement membrane to the abluminal side at approximately 20% the rate of water flow from the abluminal side to the epithelial basement membrane side of the matrix. UBM also has viscoelastic properties.

UBM can be sterilized by any of a number of standard methods without loss of its ability to induce endogenous tissue growth. For example, the material, after rinsing in saline and peracetic acid at 0.05% to 1.0%, can be sterilized by ethylene oxide treatment, gamma irradiation treatment (0.5 to 2.5 mRad), gas plasma sterilization, or e-beam treatment. The material can also be sterilized by treatment with glutaraldehyde that causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods.

The following examples will serve to better demonstrate the successful practice of the present invention.

Exemplification

As exemplification of the utility of methods and compositions of the invention, UBM is applied to heart valve defects. As will be appreciated by those of ordinary skill in the art, methods and compositions disclosed herein are applicable to other tissue regenerative compositions derived from sources of epithelial tissue other than the urinary bladder, from mammalian sources other than pigs, and to tissue defects other than heart valve. Moreover, tissue regenerative composition of the invention can be applied in a form other than a sheet or multilayer sheet of material, for example, UBM may be applied as an extract, in gel form, powdered form, tubular form, sheet form, or as strips, cords or struts or mixed with other pharmaceutical agents, for example, growth factors and gene products. UBM may be extruded or molded in or on a form to fit a particular application in the body. The preparation of fluidized forms of tissue is described in U.S. Pat. No. 5,275,826, the disclosure of which is incorporated herein by reference, and the preparation of solid sheets and strips of tissue is described in U.S. Pat. No. 5,711,969, the disclosure of which is incorporated herein by reference.

Application 1: Cardiac Tissue Repair

One embodiment, according to the invention, is a tissue regenerative composition for repair or replacement of cardiac tissues. Cardiac tissues include, but are not limited to, diseased, damaged, or missing heart tissue including myocardium, epicardium, endocardium, pericardium, interatrial and interventricular septum and all heart valves and associated valve leaflets including pulmonic valve, aortic valve, right atrioventricular valve and left atrioventricular valve and portions of adjacent vessels of the heart including pulmonary artery, pulmonary vein, aorta, inferior vena cava, and superior vena cava.

In this embodiment of the invention disclosed herein, UBM was prepared from porcine urinary bladder as described above, and used as autogenic and xenogenic anterior heart valve replacement leaflet of the pulmonic valve in five pigs and three dogs.

UBM, configured as a single sheet of material or as double thickness material, was cut with scissors or a scalpel at the time of surgery to fit the pulmonic valve anterior leaflet. UBM was sutured directly to the annulus at the base of the valve. In the single sheet embodiment, the epithelial basement membrane side of UBM was positioned on the right ventricular luminal side of the replacement valve leaflet and sutured directly to the annulus of the pulmonic valve. In a double thickness embodiment of UBM, UBM was folded so that the epithelial basement membrane was positioned on both surfaces, i.e., ventricular and arterial surfaces, of the replacement pulmonic valve leaflet, and sutured directly to the annulus of the pulmonic valve.

The pulmonic valves of experimental dogs and pigs were examined 6 and 12 weeks after valve replacement. One dog was examined at 5 months after valve leaflet replacement. Standard tissue fixation and histopathological techniques were used to examine the harvested valve leaflets.

At six weeks post valve leaflet replacement, epithelialization of the replacement valve leaflet was present over the entire valve leaflet surface. Cells migrating over the valve leaflet surface stained positive by immunofluorescent staining for von Willebrand factor indicating that these cells were of endothelial origin. In some valve leaflets some of the endothelial cells had features of early progenitor cells. Neovascularization, endothelial cell infiltration, and deposition of extracellular matrix were observed originating from the host tissue at the annulus of the pulmonic valve and extending into the replacement valve leaflet.

At twelve weeks and at five months post valve leaflet replacement, none of the original UBM tissue composition was recognizable and restoration of the valve leaflet was complete. Unexpected findings at all time points examined included lack of endothelial invasion into the replacement valve leaflet, lack of thrombosis, and lack of calcification or cell-mediated rejection of the replacement valve leaflet. Moreover, the shape of the replacement valve leaflet was unchanged from the shape of the original valve leaflet, at all time points examined.

Ultrasound studies of the pulmonic valve in pigs at 8, 12, 16 and 20 weeks after valve replacement demonstrated a competent valve.

In another embodiment of this aspect of the invention, fluidized, powderized, or pulverized forms of UBM are applied to or injected into or adjacent to diseased or defective cardiac tissue to promote endogenous tissue repair. For example, fluidized UBM is injected into or adjacent to a congenital interventricular septal defect, congenital interatrial septal defect, or into the lumen of a patent ductus arteriosus to promote endogenous growth of tissue in these areas.

Application of UBM to cardiac tissues is accomplished by the application of several different surgical approaches. For example, a minimal invasive procedure is used to approach the cardiac surgical site with the aid of a laproscope. Alternatively, a thoracotomy is performed. UBM is brought to the surgical site in any of its prepared forms such as a sheet, loop, strip or as an injectable, powered, or pulverized form. Sheets or strips of UBM are custom-fit for the particular cardiac application before or during the surgical procedure. Sheets or strips of UBM are secured adjacent to or in the defective or diseased cardiac tissue with sutures, staples, tissue glue, or any other means known to one skilled in the art.

Application 2: Matrix for In Vitro Cell Proliferation

Human microvascular endothelial cells (HMVEC) form endothelium, a single layer of cells organized on a basement membrane in vivo in a manner that mimics epithelium. Studies were conducted in vitro using isolated HMVEC plated on (i) the epithelial basement membrane side of a sheet of UBM, (ii) the abluminal surface of UBM, (iii) small intestine submucosa tissue graft composition (SIS) prepared according to the methods disclosed in the '508 and '178 patents, and (iv) urinary bladder submucosa tissue composition (UBS) prepared according the method disclosed in the '389 patent.

HMVEC grew into the matrix and did not form a confluent cell layer following three days' growth when plated on the surface of SIS and UBS regardless of whether HMVEC were plated on the luminal or abluminal surface of SIS or UBS.

HMVEC plated on the abluminal surface of UBM grew into the matrix, proliferated and differentiated into mature endothelial cells. Like HMVEC plated on the abluminal surface of SIS and UBS, a confluent layer of HMVEC was not formed on the abluminal surface of UBM following three days' growth.

In contrast to other previously known tissue regenerative compositions such as SIS and UBS in these studies, HMVEC plated on the epithelial basement membrane side (luminal) of a sheet of UBM attached to UBM, proliferated, differentiated and formed a confluent monolayer following three days' growth.

Application 3

It is contemplated that the tissue graft composition of the present invention can be used to induce repair or replacement of tissue in vivo, including connective tissues, such as ligaments, tendons, cartilage, bone, joints, and muscle, epithelial tissues, such as urinary bladder, and other tissues of the urogenital tract, stomach, esophagus, and other tissues of the gastrointestinal tract, liver, nervous tissue, tissues of the head and neck, skin, and other tissues using the same procedures described in U.S. Pat. Nos. 4,902,508; 4,956,178; 5,281,422; 5,352,463; 5,554,389; 5,275,826; 4,902,508; 5,372,821; 5,445,833; 5,516,533; 5,573,784; 5,641,518; 5,695,998; 5,711,969; 5,755,791; 5,762,966; and 5,885,619, the disclosures of which are incorporated herein by reference. The tissue graft composition of the invention can also be used with synthetic or non-synthetic polymers for restoration of tissues.

I claim:

1. A matrix, comprising:
   a devitalized mammalian epithelial basement membrane of the urinary bladder and tunica propria immediately subjacent to said basement membrane wherein said matrix induces restoration, remodeling, or repair of nervous tissue when placed in contact with diseased, damaged, or defective nervous tissue.

2. The matrix of claim 1 wherein said matrix is shaped to conform to said diseased, damaged, or defective nervous tissue.

3. The matrix of claim 1 wherein said matrix comprises an injectable form of said matrix.

4. The matrix of claim 1 wherein said matrix further comprises a pharmaceutical agent.

5. The matrix of claim 1 wherein said nervous tissue is at least a portion of the peripheral nervous system.

6. The matrix of claim 1 wherein said nervous tissue is at least a portion of the central nervous system.

7. The matrix of claim 1 wherein said matrix is shaped to conform to missing nervous tissue.

8. The matrix of claim 1 wherein said matrix comprises a soluble form of said matrix.

9. The matrix of claim 1 wherein said matrix comprises a particulate form of said matrix.

10. The matrix of claim 1 wherein said matrix comprises a gel form of said matrix.

11. The matrix of claim 1 wherein said matrix comprises a lyophilized form of said matrix.

12. The matrix of claim 1 wherein said matrix comprises a dehydrated form of said matrix.

13. The matrix of claim 1 wherein said matrix comprises a gene product.

14. A method for inducing restoration of nervous tissue in a mammal, said method, comprising:
    contacting a matrix comprising at least a portion of devitalized mammalian epithelial basement membrane of the urinary bladder with diseased, defective, or damaged nervous tissue, wherein said matrix induces restoration, restoration or repair of said nervous tissue.

15. The method of claim 14 wherein said matrix further comprises the tunica propria of the urinary bladder.

16. A composition, comprising:
    at least a portion of devitalized epithelial basement membrane and tunica propria of a mucosa delaminated from a mammalian epithelial tissue and shaped to conform to diseased, damaged, or defective nervous tissue.

17. The composition of claim 16 further comprising submucosa.

18. The composition of claim 16 further comprising at least a portion of the tunica muscularis.

19. The composition of claim 16 said diseased, damaged, or defective nervous tissue comprises at least a portion of the peripheral nervous system.

20. The composition of claim 16 wherein said diseased, damaged, or defective nervous tissue comprises at least a portion of the central nervous system.

21. A matrix for restoring, remodeling, replacing or repairing nervous tissue, comprising:

a devitalized mammalian epithelial basement membrane of the urinary bladder and tunica propria immediately subjacent to said basement membrane.

22. The matrix of claim 21 wherein the matrix further comprises at least a portion of tunica muscularis.

23. The matrix of claim 21 wherein the matrix further comprises at least a portion of submucosa.

24. The matrix of claim 21 wherein said matrix further comprises a synthetic or non-synthetic polymer.

25. The matrix of claim 21 wherein said matrix further comprises a cell.

26. A method for restoring, remodeling, replacing or repairing nervous tissue in a mammal, said method comprising:

applying a matrix comprising at least a portion of devitalized epithelial basement membrane of a mammalian urinary bladder in the mammal having a diseased, defective, or damaged nervous tissue.

27. The method of claim 26 wherein said matrix further comprises at least a portion of the tunica propria.

28. The method of claim 26 wherein said matrix further comprises at least a portion of the tunica muscularis.

29. The method of claim 26 wherein said matrix further comprises at least a portion of the submucosa.

30. A composition for restoring, remodeling, replacing or repairing nervous tissue in a mammal, comprising:

at least a portion of devitalized epithelial basement membrane and tunica propria delaminated from epithelial tissue of a mammalian urinary bladder.

31. The composition of claim 30 further comprising at least a portion of submucosa.

32. The composition of claim 30 further comprising at least a portion of the tunica muscularis.

33. A method of manufacture of a tissue graft composition, comprising:

deepithelializing a mammalian epithelial tissue by placing the tissue in a hypertonic saline solution to form a devitalized composition comprising an epithelial basement membrane.

34. The method of claim 33, wherein the tissue is urinary bladder.

35. The method of claim 33, wherein the tissue is intestine.

* * * * *